(12) United States Patent
Oswald et al.

(10) Patent No.: US 11,725,160 B2
(45) Date of Patent: Aug. 15, 2023

(54) SULFUR-CONTAINING VOLATILE ORGANIC COMPOUNDS IN CANNABIS

(71) Applicant: ABX INVESTMENTS, INC., Irvine, CA (US)

(72) Inventors: Iain W.H. Oswald, Irvine, CA (US); Kevin A. Koby, Irvine, CA (US); Thomas J. Martin, Jr., Irvine, CA (US)

(73) Assignee: ABX INVESTMENTS, INC., Tustin, CA (US)

( * ) Notice: Subject to any disclaimer, the term of this patent is extended or adjusted under 35 U.S.C. 154(b) by 123 days.

(21) Appl. No.: 17/154,770

(22) Filed: Jan. 21, 2021

(65) Prior Publication Data
US 2021/0253976 A1    Aug. 19, 2021

Related U.S. Application Data

(60) Provisional application No. 63/005,678, filed on Apr. 6, 2020, provisional application No. 62/963,615, filed on Jan. 21, 2020.

(51) Int. Cl.
*C11B 9/00* (2006.01)
*G01N 30/74* (2006.01)
(Continued)

(52) U.S. Cl.
CPC ............... *C11B 9/0011* (2013.01); *A23L 2/56* (2013.01); *A23L 27/203* (2016.08); *A23L 27/2022* (2016.08); *A23L 27/2052* (2016.08); *A24B 15/167* (2016.11); *C11B 9/0007* (2013.01); *C12C 5/026* (2013.01); *G01N 30/7206* (2013.01); *G01N 30/74* (2013.01); *G01N 30/8624* (2013.01); *G01N 33/0098* (2013.01);
(Continued)

(58) Field of Classification Search
CPC ............... A23L 27/2022; A23L 27/203; A23L 27/2052; A23L 2/56; A24B 15/167; C12C 5/026; A23V 2002/00
USPC ........................................................ 426/535
See application file for complete search history.

(56) References Cited

U.S. PATENT DOCUMENTS

2020/0035121 A1* 1/2020 Pandolfino ............... A24D 1/18
2021/0068444 A1* 3/2021 Alarcon .................. A24F 40/20

OTHER PUBLICATIONS

"What is Skunked Beer?" CulinaryLore, Jun. 7, 2016, available at https://culinarylore.com/drinks:what-is-skunked-beer/ (last accessed Aug. 10, 2022) (5 pages).†
(Continued)

*Primary Examiner* — Brent T O'Hern
(74) *Attorney, Agent, or Firm* — Foley & Lardner LLP

(57) ABSTRACT

An edible composition, an aerosol composition, a flavor composition, a fragrance composition, or an inhalable composition includes an organosulfur compound such as prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, dimethyl sulfide, or a combination of any two or more thereof, and a primary terpene compound selected from the group consisting of myrcene, β-caryophyllene, limonene, α-pinene, β-pinene, valencene, ocimene, terpinolene, or a combination of any two or more thereof.

12 Claims, 9 Drawing Sheets

Prenyl Mercaptan   2-Methylthiophene   3-Methylthiophene

Diprenyl Disulfide   Prenylmethylthiol (1-(methylsulfanyl)-3-methyl-2-butene)

3-Methyl-1-[(3-methyl-2-buten-1-yl)sulfanyl]-2-butene   Prenyl thioacetate

Dimethyl Disulfide   Thiogeraniol   Dimethyl Sulfide

(51) Int. Cl.
- G01N 30/72 (2006.01)
- G01N 33/00 (2006.01)
- G01N 30/86 (2006.01)
- A23L 27/20 (2016.01)
- C12C 5/02 (2006.01)
- A23L 2/56 (2006.01)
- A24B 15/167 (2020.01)
- G01N 30/02 (2006.01)

(52) U.S. Cl.
CPC .... *A23V 2002/00* (2013.01); *G01N 2030/025* (2013.01)

(56) References Cited

OTHER PUBLICATIONS

Rice et al., "Characterizing the Smell of Marijuana by Odor Impact of Volatile Compounds: An Application of Simultaneous Chemical and Sensory Analysis," PLoS One, vol. 10, No. 12, DOI:10.1371/journal.pone.0144160 (Dec. 10, 2015) (17 pages).†

Cannon et al., "Volatile sulfur compounds in tropical fruits," J. Food Drug Anal., vol. 26, pp. 445-468 (Feb. 16, 2018).†

McGorrin, "The Significance of Volatile Sulfur Compounds in Food Flavors." Chapter 1, pp. 3-31, in Volatile Sulfur Compounds in Food, Qian et al., Ed., ACS Symposium Series, DOI:10.10,21/bk-2011-1068.ch001, Aug. 24, 2011.†

Terpenes &Testing Magazine, Jan./Feb. 2019, MACE Media Group, available at https://terpenesandtesting.com/terpenes-testing-magazine-jan-feb-2019-issue (60 pages).†

Terpenes &Testing Magazine, Sep./Oct. 2019, MACE Media Group, available at https://terpenesandtesting.com/magazine-sep-oct-2019/ (36 pages).†

Terpenes &Testing Magazine, Jan./Feb. 2020, MACE Media Group, available at https://terpenesandtesting.com/terpenes-testing-magazine-jan-feb-2020-issue (28 pages).†

Oswald et al. "Identification of a New Family of Prenylated Volatile Sulfur Compounds in Cannabis Revealed by Comprehensive Two-Dimensional Gas Chromatoaraphy," ACS Omega, vol. 6, No. 57, pp. 31667-31676 (Nov. 12, 2021).†

\* cited by examiner
† cited by third party

Prenyl Mercaptan

2-Methylthiophene

3-Methylthiophene

Diprenyl Disulfide

Prenylmethylthiol (1-(methylsulfanyl)-3-methyl-2-butene

3-Methyl-1-[(3-methyl-2-buten-1-yl)sulfanyl]-2-butene

Prenyl thioacetate

Dimethyl Disulfide

Thiogeraniol

Dimethyl Sulfide

SULFUR-CONTAINING VOLATILE ORGANIC COMPOUNDS IN CANNABIS

CROSS REFERENCE TO RELATED APPLICATIONS

This application claims the benefit of U.S. Provisional Application No. 62/963,615, filed Jan. 21, 2020, and U.S. Provisional Application No. 63/005,678, filed Apr. 6, 2020, the disclosures of each of which are incorporated herein by reference in their entirety.

FIELD

The present invention relates to various compositions, products, and methods that are capable of, or adapted to, providing, augmenting, or enhancing the gassy odor or aroma. In particular, the present invention relates to organosulfur compound containing compositions products, and methods that are capable of, or adapted to, providing, augmenting, or enhancing the gassy odor or aroma.

BACKGROUND

The following discussion is provided to aid the reader in understanding the disclosure and is not admitted to describe or constitute prior art thereto.

Cannabis is one of the most popular recreational drugs and it has recently seen significant changes to its legality within the United States and other countries. The Cannabis plant has many unique traits, such as its ability to biosynthesize a wide variety of secondary metabolites including tetrahydrocannabinol (THC), cannabidiol (CBD), as well as a plethora of monoterpenes, monoterpenoids, sesquiterpenes, and sesquiterpenoids. Although typically consumed for the psychoactive effects brought upon by THC, and more recently proposed therapeutic effects of CBD, recent interest within the greater cannabis community has turned to terpenes and other compounds that give cannabis its unique scent and flavor. Like THC and CBD, the concentrations and types of terpenoids present are heavily influenced by both genetics and external stress on the plant throughout the growth cycle. Through selective breeding, growers have been able to produce plants with a wide variety of aromas, all primarily due to the presence of compounds of the terpene class.

The major or primary aroma compounds contributing to the odor of cannabis as described in scientific and popular literature are β-Myrcene, α- and β-Pinene, D-Limonene, β-Caryophyllene, Terpinolene, and Humulene, although over 200 compounds have been described throughout the scientific literature. The presence of various secondary metabolites, terpenes, terpenoids, sesquiterpenes, and sesquiterpenoids results in Cannabis products having a wide variety of aromas and flavors with remarkable depth and complexity. One of the most popular organoleptic descriptors in Cannabis is the presence of a "Gassy" aroma—that is, an aroma that emulates that of gasoline. This aroma is described as a piercing, sulfuric, sharp odor on the nose that is often associated strongly with strains of the OG family, although other families can likewise have similar odors. It is also commonly considered an indicator of freshness and/or quality of a cannabis product. Although cannabis breeders can breed plants to express specific odors, such as this odor, the exact chemical composition that leads to it is unknown. Within the cannabis community, much focus has been on terpenes, sesquiterpenes, and their oxygenated derivatives. However, attempts at emulating certain aromas using artificial blends with many of these compounds in ratios determined from gas chromatographic data have fallen short when capturing the complete aroma profile of a given cannabis strain. One strain family that has been notoriously difficult to emulate is the OG family, pioneered by the strain OG Kush. This strain is characterized by what is often described as the quintessential aroma of cannabis—a strong, sulfuric, gassy odor that has a high substantivity—the ability for an odor to be detectable over a period of time. This strain has subsequently been cross-bred with other strains, leading to a plethora of strains that now possess this pungent odor. Attempts at using chemical characterization methods such as gas or liquid chromatography have not led to an obvious origin of this odor in cannabis, and thus remains somewhat of a mystery regarding what compound, or compounds, contribute.

SUMMARY

According to a first aspect, a composition comprises an organosulfur compound selected from the group consisting of prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, dimethyl sulfide, or a combination of any two or more thereof, and a primary terpene compound selected from the group consisting of myrcene, β-caryophyllene, limonene, α-pinene, β-pinene, valencene, ocimene, terpinolene, or a combination of any two or more thereof, wherein the composition is an edible composition, an aerosol composition, a flavor composition, a fragrance composition, or an inhalable composition.

In certain embodiments, the composition comprises about 0.000001 wt % to about 0.3 wt % of the organosulfur compound, based on the total weight of the composition. In certain embodiments, the organosulfur compound comprises prenyl mercaptan, prenyl thioacetate, or 2-methylthiophene.

In certain embodiments, the primary terpene compound is present in an amount of from about 0.1 wt % to about 99 wt %, based on the total weight of the composition. In certain embodiments, the primary terpene compound is present in an amount of from about 0.1 wt % to about 90 wt %, based on the total weight of the composition. In certain embodiments, the composition further comprises a secondary terpene compound selected from the group consisting of humulene, linalool, bisabolol, nerol, phellandrene, terpineol, farnesene, fenchyl alcohol, geraniol, menthol, citronellol, citronellal, geranyl acetate, nerolidol, citral, or a combination of any two or more thereof. In certain embodiments, the secondary terpene compound is present in an amount of from about 0.01 wt % to about 50 wt %, based on the total weight of the composition. In certain embodiments, the composition further comprises a second flavoring and/or fragrancing agent. In certain embodiments, the second flavoring and/or fragrancing agent may be present in an amount of about 0.000001% to about 90% by weight, based on the total weight of the composition.

In certain embodiments, the composition is an edible composition. In certain embodiments, the composition is a food or beverage product. In certain embodiments, the beverage is beer, an alcohol containing beverage, or other non-alcohol containing beverage product. In certain embodiments, the composition is an inhalation composition. In certain embodiments, the composition is a flavor and/or fragrance composition.

According to a another aspect, provided is for augmenting or enhancing the gassy aroma or taste of a product, the process comprising the step of adding to said product an organosulfur compound selected from prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, and dimethyl sulfide, or a combination of any two or more thereof, wherein the product is an edible product, an aerosol product, a flavor product, a fragrance product, or an inhalable product. In certain embodiments, the product is an edible product or an inhalable product. In certain embodiments, the edible product is a food or beverage product. In certain embodiments, the beverage is beer, any alcohol containing beverage, or other non-alcohol containing beverage product.

In certain embodiments, the organosulfur compound is added in an amount of from about 0.000001 wt % to about 0.6 wt %, based on the total weight of the product. In certain embodiments of the fourth aspect, the organosulfur compound comprises from about 0.000001 wt % to about 0.3 wt % of prenyl mercaptan and from about 0.000001 wt % to about 0.3 wt % of 2-methylthiophene. In certain embodiments, the process further comprises adding a primary terpene compound selected from the group consisting of myrcene, β-caryophyllene, limonene, α-pinene, β-pinene, valencene, ocimene, terpinolene, or a combination of any two or more thereof. In certain embodiments, the primary terpene compound is added in an amount of from about 0.1 wt % to about 99 wt %, based on the total weight of the composition.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
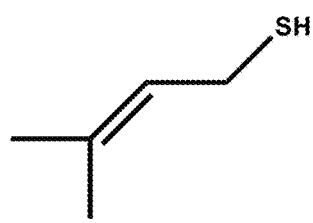
FIG. 1 represents structures of compounds discovered contributing to gas odor in cannabis.
Figure 1:
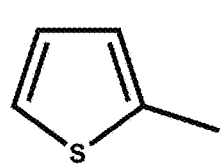
Figure 1:
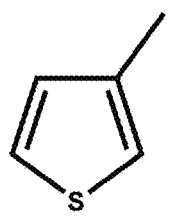
Figure 1:
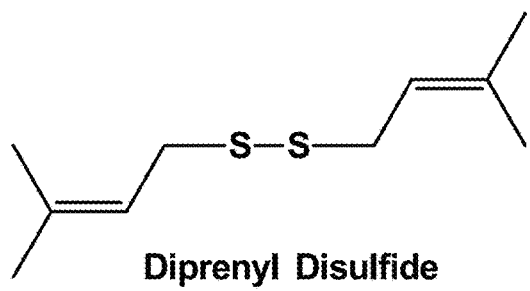
Figure 1:
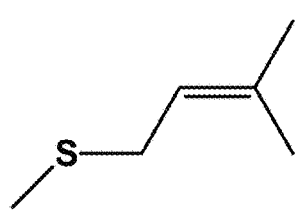
Figure 1:
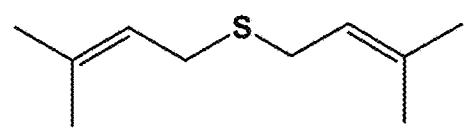
Figure 1:
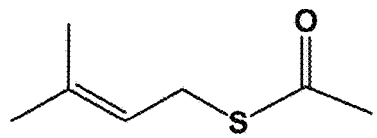
Figure 1:
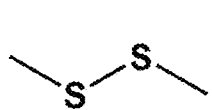
Figure 1:
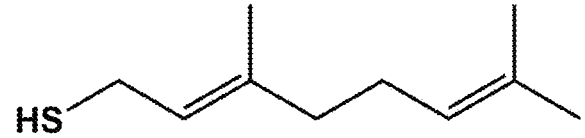
Figure 1:
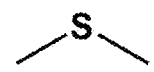

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. As a non-limiting example, a reference to "X and/or Y" can refer, in one embodiment, to X only (optionally including elements other than Y); in another embodiment, to Y only (optionally including elements other than X); in yet another embodiment, to both X and Y (optionally including other elements).

Unless indicated otherwise, reference to "percent" is to be understood as "weight percent," and reference to "ratio" is as a weight/weight ratio.

As used herein, the term "terpene compound" is understood to mean any organic compound that contains at least one isoprene subunit within its structure and their oxygenated derivatives.

As used herein, the terms "odor" and "aroma" are used interchangeably and represent the sensory attributes of certain substances perceptibly determined by the olfactory system.

As used herein, the term "flavoring agent" is understood to mean an additive that is meant to improve the taste or aroma impression of food or other substances, and can include both natural and synthetic ingredients.

As used herein, the term "gassy" is understood to be an organoleptic descriptor that represents a type of Cannabis aroma that emulates a sulfurous petroleum odor.

As used herein, the term "strain" is used to represent various chemovars or cultivars.

As used herein, the term "cultivar" represents a group of similar plants that by structural features and performance (i.e., morphological and physiological characteristics) can be identified from other varieties within the same species. Furthermore, the term "cultivar" variously refers to a variety, strain, or race of plant that has been produced by horticultural or agronomic techniques and is not normally found in wild populations. The terms cultivar, variety, strain, and race are often used interchangeably by plant breeders, agronomists, and farmers.

As used herein, the term "landrace" is used to represent a local variety of a domesticated plant species that has developed largely by natural processes, by adaptation to the natural and cultural environment in which it lives.

As used herein, the term "plant matter" is used to represent to any part of a plant including but not limited to the flower bud, leaf, petal, flower, stem, seed, embryo, shoot, root, stipule, ovule, bract, trichome, branch, petiole, internode, bark, pubescence, tiller, rhizome, frond, blade, ovule, pollen, stamen, and the like.

As used herein, the term "dry flower" is understood to mean a flower or bud of the plant matter that has been cured and dried and has less than about 0.63 water activity, or alternatively about 13% moisture by weight of the flower. Dry flower, or dry herb, is what is used for rolling into a smokable composition (i.e. a "joint") or in an edible form, for example.

In some embodiments the plant matter may be 'alive' or 'wet' which means it is not cured. Thus, the contents of various components may be measured in terms of dry flow, wet flower, extracts, or otherwise.

Various aspects and/or embodiments of this disclosure relate to compositions, products, and methods that are capable of, or adapted to, providing, augmenting, or enhancing the gassy odor or aroma. Other aspects and/or embodiments relate to plant species, cultivars, and methods of breeding plant species which include compounds capable of providing gassy odor or aroma and/or and modifying the olfactory qualities of the gassy aroma. Yet other aspects and/or embodiments relate to methods for analyzing and/or identifying the compounds that contribute to a gassy aroma associated with a product.

Provided herein are compositions comprising organosulfur compounds that are capable of providing a gassy aroma and/or and modifying the olfactory qualities of the gassy aroma. The organosulfur compounds include known organosulfur compounds, such as for example and without limitation, mercaptans, thiols, sulfides, disulfides, polysilfides, and thioesters that contribute to or enhance the desired aroma and/or olfactory qualities of the composition. Suitable organosulfur compounds, include, but are not limited to, prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, and dimethyl sulfide. In certain embodiments, the organosulfur compound includes prenyl mercaptan, 2-methylthiophene, 3-methylthiophene, or a combination of any two or more thereof. In certain embodiments, the organosulfur compound includes prenyl mercaptan, 2-methylthiophene, prenyl thioacetate or a combination of any two or more thereof. In certain embodiments, the organosulfur compound includes prenyl mercaptan, 2-methylthiophene, dimethyl disulfide, prenyl thioacetate or a combination of any two or more thereof. Any combination of the organosulfur compounds disclosed here can be included in the compositions. Structures of illustrative organosulfur compounds that contribute to the desirable odor, e.g., gassy odor in cannabis are illustrated in FIG. 1.

In certain embodiments, the organosulfur compounds may be present at up to about 5% by weight of the total composition, up to about 2%, up to about 1%, up to about 0.6%, up to about 0.3%, up to about 0.2% or up to about 0.1% by weight of the total weight of the composition. For example, the organosulfur compounds are present in the composition from at least about 0.0000001% by weight of the total composition, at least about 0.000001%, at least about 0.00001%, at least about 0.0001%, at least about 0.001%, at least about 0.01%, at least about 0.05% or at least about 0.1% by weight. This includes where the organosulfur compound is present from about 0.0000001% to about 10% of the total weight of the composition, including without limitation, about 0.00001% to about 5%, about 0.0001% to about 3%, about 0.001% to about 2%, or about 0.01% to about 1% of the total weight of the composition, about 0.0000001% to about 0.5%, about 0.0000001% to about 0.2%, about 0.0000001% to about 0.1%, or any range including and/or in-between any two of these values. In certain embodiments, the organosulfur compound is from about 0.000001 wt % to about 0.3 wt % of the total weight of the composition.

The composition may include about 0.000001 wt % to about 0.3 wt % of the total weight of the composition, of prenyl mercaptan. In certain embodiments, the composition includes about 0.000001 wt % to about 0.3 wt % of the total weight of the composition, of 2-methylthiophene. In certain embodiments, the composition includes about 0.000001 wt % to about 0.25 wt % of the total weight of the composition, of prenyl mercaptan and about 0.000001 wt % to 1.00 wt % of the total weight of the composition, of 2-methylthiophene. In certain embodiments, the composition includes about 0.000001 wt % to about 0.3 wt % of the total weight of the composition, of 3-methylthiophene. In certain embodiments, the composition includes about 0.000001 wt % to about 0.3 wt % of the total weight of the composition, of dimethyl disulfide. In certain embodiments, the composition includes about 0.000001 wt % to about 0.3 wt % of the total weight of the composition, of diprenyl disulfide. In certain embodiments, the composition includes about 0.000001 wt % to about 0.3 wt % of the total weight of the composition, of 3-methyl-2-buten-1-yl thiolacetate. In certain embodiments, the composition includes about 0.000001 wt % to about 0.3 wt % of the total weight of the composition, of 3-methyl-1-[(3-methyl-2-buten-1-yl)sulfanyl]-2-butene. In certain embodiments, the composition includes about 0.000001 wt % to about 0.3 wt % of the total weight of the composition, of prenylmethylthiol (1-(methylsulfanyl)-3-methyl-2-butene). In certain embodiments, the composition includes about 0.000001 wt % to about 0.3 wt % of the total weight of the composition, of prenyl thioacetate. In certain embodiments, the composition includes about 0.000001 wt % to about 0.3 wt % of the total weight of the composition, of thiogeraniol. In certain embodiments, the composition includes about 0.000001 wt % to about 0.3 wt % of the total weight of the composition, of dimethyl sulfide. Various combinations of organosulfur compounds may also be used in the compositions. For example, prenyl mercaptan may be combined with other organosulfur compounds in suitable amounts to provide the desired gassy aroma profile. Likewise, combinations of other organosulfur compounds described herein may also be used in the concentration ranges described herein. Thus, in certain embodiments, the composition includes about 0.000001 wt % to about 0.3 wt % of the total weight of the composition, of prenyl mercaptan and 0.000001 wt % to about 0.3 wt % of the total weight of the composition, of prenyl thioacetate.

In addition to the organosulfur compounds, in certain embodiments, the compositions may include one or more terpene compounds. Non-limiting examples of terpene compounds include hemiterpenes, monoterpenes, sesquiterpenes, diterpenes, sesterterpenes, triterpenes, sesquarterpenes, tetraterpenes, polyterpenes, terpenoids and norisoprenoids. Suitable terpene compounds may include a primary terpene compound and a secondary terpene compound. Illustrative primary and secondary terpene compounds include, but are not limited to, myrcene, β-caryophyllene, α or β-Pinene, α or β-phellandrene, limonene, terpinolene, linalool, pinene, terpineol, fenchyl alcohol, α-bisabolol, camphene, terpinolene, humulene, geraniol, camphor, cedrene, 1-menthol, cis-β-ocimene, trans-β-ocimene, terpinene, delta-3-carene, isoborneol, nerol, valencene, farnesene (t), fenchone, ocimene, bergotamene, thujene, ylangene, sabinene hydrate, and the like, or a combination of any two or more thereof. Many other terpenes are known in the art and commercially available, and can be used in the compositions.

In certain embodiments, the primary terpene compounds may include, but are not limited to, myrcene, β-caryophyllene, limonene, α-pinene, β-pinene, valencene, ocimene and terpinolene, and the like, or a combination of any two or more thereof. In certain embodiments, the primary terpene compounds constitute a major amount of the total terpene content or is a major contributor to the resulting aroma of the composition. In certain embodiments, the primary terpene compounds constitute at least about 5% by weight of the total composition, at least about 10%, at least about 20%, at least about 30%, at least about 40%, at least about 50%, at least about 60%, at least about 70%, at least about 80% or at least about 90% by weight. In certain embodiments, the primary terpene compounds constitute up to about 99.99% by weight of the total composition, up to about 99%, up to about 95%, up to about 92%, up to about 90%, up to about 85% or up to about 80% by weight of the total weight of the composition. In certain embodiments, the primary terpene compound constitutes about 5% to about 99.99% of the total weight of the composition, including without limitation, about 10% to about 98%, about 20% to about 98%, about 30% to about 98%, about 40% to about 98%, about 50% to about 95%, about 60% to about 90%, or about 70% to about 85% of the total weight of the composition, or any range including and/or in-between any two of these values.

In certain embodiments, the primary terpene compound is present in an amount of from about 0.1 wt % to about 90 wt %, based on the total weight of the composition. In certain embodiments, the composition includes about 0.1 wt % to about 90 wt % of the total weight of the composition, of myrcene. In certain embodiments, the composition includes about 0.1 wt % to about 90 wt % of the total weight of the composition, of β-caryophyllene. In certain embodiments, the composition includes about 0.1 wt % to about 90 wt % of the total weight of the composition, of limonene. In certain embodiments, the composition includes about 0.1 wt % to about 90 wt % of the total weight of the composition of α-pinene. In certain embodiments, the composition includes about 0.1 wt % to about 90 wt % of the total weight of the composition of β-pinene. In certain embodiments, the composition includes about 0.1 wt % to about 90 wt % of the total weight of the composition of valencene. In certain embodiments, the composition includes about 0.1 wt % to about 90 wt % of the total weight of the composition of ocimene. In certain embodiments, the composition includes about 0.1 wt % to about 90 wt % of the total weight of the composition of terpinolene.

In certain embodiments, the compositions include a secondary terpene compound. In certain embodiments, the secondary terpene compounds may include, but are not limited to, humulene, linalool, α-bisabolol, nerol, α-phellandrene, α-terpineol, farnesene, fenchyl alcohol, geraniol, menthol, citronellol, citronellal, geranyl acetate, nerolidol, citral, and the like, or a combination of any two or more thereof. In certain embodiments, the secondary terpene compounds constitute a minor amount of the total terpene content or is a minor contributor to the resulting aroma of the composition. In certain embodiments, the secondary terpene compounds constitute up to about 30% by weight of the total composition, up to about 20%, up to about 10%, up to about 5%, up to about 2%, up to about 1% or up to about 0.1% by weight of the total weight of the composition. In certain embodiments, the secondary terpene compounds constitute at least about 0.0001% by weight of the total composition, at least about 0.001%, at least about 0.01%, at least about 0.1%, at least about 0.5%, at least about 1% or at least about 2% by weight. In certain embodiments, the secondary terpene compound constitutes about 0.0001% to about 30% of the total weight of the composition, including without limitation, about 0.001% to about 25%, about 0.1% to about 20%, about 1% to about 10%, or about 2% to about 5% of the total weight of the composition, or any range including and/or in-between any two of these values. In certain embodiments, the secondary terpene compound is present in an amount of from about 0.01 wt % to about 10 wt %, based on the total weight of the composition In certain embodiments, the secondary terpene compound is present in an amount of from about 0.1 wt % to about 30 wt %, based on the total weight of the composition. In certain embodiments, the composition includes about 0.1 wt % to about 30 wt % of the total weight of the composition, of one or more secondary terpenes selected from humulene, linalool, α-bisabolol, nerol, α-phellandrene, α-terpineol, farnesene, fenchyl alcohol, geraniol, menthol, citronellol, citronellal, geranyl acetate, nerolidol and citral.

In certain embodiments, the composition includes about 0.000001 wt % to about 0.3 wt % of prenyl mercaptan and about 0.1 wt % to 90 wt % myrcene, based on the total weight of the composition. In certain embodiments, the composition includes about 0.000001 wt % to about 0.3 wt % of prenyl mercaptan, about 0.1 wt % to 90 wt % myrcene, and about 0.1 wt % to 90 wt % D-limonene, based on the total weight of the composition. In certain embodiments, the composition includes about 0.000001 wt % to about 0.3 wt % of prenyl mercaptan, about 0.1 wt % to 90 wt % myrcene, about 0.1 wt % to 90 wt % of D-limonene, and about 0.1 wt % to 90 wt % of β-Caryophyllene based on the total weight of the composition. In certain embodiments, the composition includes about 0.000001 wt % to about 0.3 wt % of prenyl mercaptan, about 0.000001 wt % to about 0.3 wt % of 2-methylthiophene, about 0.1 wt % to 90 wt % myrcene, about 0.1 wt % to 90 wt % of D-limonene, and about 0.1 wt % to 90 wt % of β-Caryophyllene based on the total weight of the composition.

In another aspect, the composition can be formulated to have various applications. In a non-limiting way, the composition can be an edible composition, an aerosol composition, a flavor composition, a fragrance composition, or an inhalable composition. In certain embodiments, an edible product comprising a composition described herein is provided. In certain embodiments, the composition is an edible composition. In certain embodiments, the composition is an aerosol composition. In certain embodiments, the composition is a flavor composition. In certain embodiments, the composition is a fragrance composition. In certain embodiments, the composition is an inhalable composition.

The compositions may further include suitable second flavoring and/or fragrancing agents including, but not limited to, ethyl butyrate, ethyl isovalerate, methyl anthranillate, vanillin, ethyl maltol, maltol, strawberry furanone (4-OH-2,5-dimethyl-3-furanone), raspberry ketone (anisyl acetone), isoamyl acetate, isoamyl butyrate, ethyl caproate, octanal, octanol, aldehyde c-16, allyl caproate, ortho-tolualdehyde, benzaldehyde, sweet almond oil, bitter almond oil, beta-ionone, hexyl butyrate, hexyl acetate, hexyl hexanoate, propyl caproate, folione, citronellyl formate, 2-phenylpropyl isobutyrate, propionyl thiazole, methional, methyl heptadienone, gamma decalactone, melonal, passifloran, methyl-2 butyl acetate, lime terpenes, peppermint oil, orange oil, and the like, or a combination of any two or more thereof. Additional examples of flavoring agents include ingredients that are "generally recognized as safe" ("GRAS") by the United States Food and Drug Administration ("FDA"), for example, those listed as approved under 21 C.F.R. §§ 172.510, 172.515, and 172.560.

In certain embodiments, the second flavoring and/or fragrancing agents, when present, constitutes about 0.000001% to about 90% by weight of the total weight of the composition, including without limitation, about 0.000001% to about 80%, about 0.000001% to about 70%, about 0.000001% to about 60%, about 0.000001% to about 50%, about 0.000001% to about 40%, about 0.000001% to about 30%, about 0.000001% to about 20%, about 0.00001% to about 15%, about 0.0001% to about 10%, about 0.001% to about 8%, about 0.01% to about 5%, about 0.1% to about 3%, or about 1% to about 2% by weight of the total weight of the composition, or any range including and/or in-between any two of these values.

Depending upon the end application, the compositions may include other ingredients, such as surfactants, co-solvents, propellants, other flavoring agents, medicinal agents, perfumes, stabilizers, thickeners, binders, preservatives, emulsifiers, essential oils, water, salt, sweeteners, gelatin, food additives, colorants, excipients, diluents, and the like or a combination of any two or more thereof.

The organosulfur compounds described herein may be used in any flavor and fragrance applications. Accordingly, in one aspect, provided herein are flavor and fragrance compositions comprising organosulfur compounds including, but not limited to, prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, dimethyl sulfide; and a terpene compound. In certain embodiments, the organosulfur compound includes prenyl mercaptan, 2-methylthiophene, 3-methylthiophene, or a combination of any two or more thereof.

In certain embodiments, the compositions may further include a cannabinoid active agent. The cannabinoid active agent may be selected from any of the known cannabinoids, including, without limitation, tetrahydrocanabinols, tetrahydrocannabinolic acids, cannabidiol, cannabidiolic acid, cannabigerolic acid, cannabigerol, cannabigerovarinic acid, cannabigerolovarin, cannabichromenic acid, cannabichromene, cannabidivarin, cannabidivarinic acid, cannabivarin, cannabivarinic acid, tetrahydrocannabivarinic acid, tetrahydrocannabivarin, cannabinolic acid, cannabinol, cannabinodiol, cannabielsoin, cannabicyclol, and cannabicitran and isomers thereof, or a combination of any two or more thereof. When used, the cannabinoid active agent is present in an amount of from about 0.05% to 99.9% by wt based on the total weight of composition, including from 0.1 to 45%, 1 to 40%, 2 to 35%, 5 to 30%, or 10 to 20% by wt, based on the total weight of the composition.

The compositions described herein may be used in a variety of products including edible products, aerosol products, fragrance products, flavor products, inhalable products, consumer products, personal care products, and household products. The organosulfur compound-containing compositions containing one or more organosulfur compounds may synergistically enhance the olfactory effects of products to closely emulate cannabis aroma and/or flavor. In certain embodiments, the organosulfur compound-containing compositions can be used as an additive to synergistically enhance the aroma and/or flavor of products such as edible products, aerosol products, fragrance products, flavor products, inhalable products, consumer products, personal care products, and household products. In certain embodiments, the edible product is a food product or a beverage product.

In another aspect, the present technology relates to various products that may include the organosulfur compound-containing compositions described herein. Illustrative products include, but are not limited to edible products, aerosol products, fragrance products, flavor products, or inhalable products. In certain embodiments, an edible product comprising a composition described herein is provided. In certain embodiments, the edible product is a food or beverage product. In certain embodiments, the beverage is beer, any alcohol containing beverage, or other non-alcohol containing beverage product. In certain embodiments, a flavor and fragrance product comprising a composition described herein is provided. In certain embodiments, an inhalation product comprising the composition described herein is provided. In certain embodiments, the inhalation product is a vaping composition. In certain embodiments, a flavor and/or fragrance delivery system comprising the composition described herein is provided.

In another aspect, an edible product or an inhalation product comprises a composition comprising an organosulfur compound selected from the group consisting of prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, and dimethyl sulfide. In certain embodiments, the composition comprise from about 0.000001 wt % to about 0.3 wt % of prenyl mercaptan, based on the total weight of the composition. In certain embodiments, the composition comprises from about 0.000001 wt % to about 0.3 wt % of 2-methylthiophene, based on the total weight of the composition. In certain embodiments, the edible product is a food or beverage product.

Other aspects of the present technology relate to Cannabis plants. The Cannabis plant may be a hybrid plant or an engineered plant, and can be produced via known methods such as seed production or asexual reproduction. In some embodiments, provided is a cannabis plant, or an asexual clone thereof, or a plant part, tissue, or cell thereof comprising an organosulfur compound content greater than 0.00001 μg/mg as measured by gas chromatography coupled with a sulfur chemiluminescence detector and calculated based on dry weight of the dried, ground flower. The gas chromatography can be one-dimensional or a two-dimensional gas chromatography coupled with a sulfur chemiluminescence detector (GCxGC-SCD). In some embodiments, organosulfur compound content is greater than about 0.00001 μg/mg, greater than about 0.0002 μg/mg, greater than about 0.0005 μg/mg, greater than about 0.0007 μg/mg, greater than about 0.001 μg/mg %, greater than about 0.005 μg/mg, or greater than about 0.01 μg/mg as measured by gas chromatography coupled with a sulfur chemiluminescence detector and calculated based on dry weight of the dried, ground cannabis flower. In some embodiments, organosulfur compound content is less than about 0.1 μg/mg as measured by gas chromatography coupled with a sulfur chemiluminescence detector and calculated based on dry weight of the dried, ground flower In some embodiments, organosulfur compound content is less than about 0.05 μg/mg, less than about 0.01 μg/mg, less than about 0.005 μg/mg, less than about 0.003 μg/mg, greater than about 0.002 μg/mg, or greater than about 0.001 μg/mg as measured by gas chromatography coupled with a sulfur chemiluminescence detector and calculated based on dry weight of the dried, ground cannabis flower.

Methods for analyzing and/or identifying the compounds that contribute to a gassy aroma associated with a product, e.g., a cannabis product, are also provided herein. The methods include analyzing the constituents of a product having a gassy aroma using various devices and methods including, but not limited to, gas chromatography/time-of-flight mass-spectrometer (GC/TOF-MS), two-dimensional gas chromatography-time of flight mass spectrometry (2DGC-TOF MS), flame ionization detector (HD), sulfur chemiluminescence detector (SCD), gas chromatography/mass spectrometry (GC/MS), gas chromatography with atomic emission detector (GC/AED), gas chromatography/flame ionization detection/olfactometry (GC/FID/olfactometry) or high performance liquid chromatography (HPLC), or a combination of any two or more thereof.

Cannabis strains and compositions with varying degrees of gassy aroma may be analyzed using 2-dimensional gas chromatography equipped with a time-of-flight mass-spectrometer (TOF-MS), flame ionization detector (FID), and a sulfur chemiluminescence detector (SCD). It has now been surprisingly and unexpectedly discovered that a correlation exists between the organoleptic response, i.e. how 'gassy' a given strain smells to the human nose, and the concentration of certain organosulfur compounds. Such organosulfur compounds may include, but are not limited to, prenyl mercaptan (3-methylbut-2-ene-1-thiol), 2-methylthiophene, 3-methylthiophene, dimethyl disulfide, diprenyl disulfide, 3-methyl-2-buten-1-yl thioacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol ((E)-3,7-dimethyl-2,6-octadien-1-thiol), and dimethyl sulfide. It was discovered that the odors of these organosulfur compounds coupled with terpene compounds present in a strain may yield the particular 'flavor' of the gas present. Although low in relative concentration compared to the terpenes, the organosulfur compounds were found to have a significant impact on aroma and flavor. The methods for identification and analysis of the odor-producing compounds described herein can advantageously be used to guide cultivators for targeting and producing plants, clones, or plant cells with or without specific aromas associated with them, as well as develop formulations of food and beverages when targeting a unique gassy aroma or odor.

One aspect of the present technology relates to a method for detecting sulfur-containing compounds in a cannabis plant by analyzing the headspace gas from a cannabis sample using a gas chromatography. The gas chromatography can be a one- or two-dimensional gas chromatograph coupled a sulfur chemiluminescence detector (SCD). The SCD can be used in conjugation with other detectors such as a flame ionization detector (FID), a mass spectrometer (MS), nitrogen chemiluminescence detector (NCD), a nitrogen phosphorus detector (NPD), an atomic emission detector (AED), a flame photometric detector (FPD), or an electron capture detector (ECD). Suitable samples of the cannabis plant material can be placed in a bottle and the gases in a headspace bottle, can be collected using headspace tools and injected into a gas chromatography-sulfur chemiluminescence detector combined device, using an inert gas such as nitrogen as carrier gas for the gas chromatography, and performing qualitative and quantitative detection through a sulfur chemiluminescence detector. The cannabis samples can be incubated and agitated at suitable temperature (e.g., 40-150° C.) prior to collection of the headspace gas sample. In some embodiments, the cannabis sample may include cannabis flower material, such as dried flower, dried, and ground flower, a wet flower, or a flower extract. In some embodiments, the flower material may be cured. In some embodiments, the flower material may be uncured.

Instrument parameters that can be used in a 2-dimensional gas chromatographic system include using a BPX5 (5% Phenyl Polysilphenylene-siloxane) first dimension column and a high polarity MEGA-WAX (Polyethylene glycol (PEG)) secondary column.

A suitable instrument temperature ramp method may include: an initial temperature of 45° C., the temperature is maintained for 5 min, the temperature is increased to 90° C. at the speed of 5° C./min, then the temperature is increased to 130° C. at the speed of 2° C./min, the temperature is increased to 240° C. at the speed of 5° C./min, and the temperature is maintained for 1 min;

Suitable instrument parameters include:
sample inlet temperature: 200° C.;
SCD plasma Burner temperature: 800° C.;
SCD Base temperature: 250° C.;
Oxidizer flow ($O_2$): 11.50 mL/min,
Upper $H_2$ flow: 38.00 mL/min; and
Upper $H_2$ flow: 8.00 mL/min.

Illustrative sulfur-containing compounds which may be detected or identified using the gas chromatography-sulfur chemiluminescence detector method, may include, but are not limited to, prenyl mercaptan (3-methylbut-2-ene-1-thiol), 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol ((E)-3,7-dimethyl-2,6-octadien-1-thiol), and dimethyl sulfide.

Another aspect of the present technology relates to a process for augmenting or enhancing the gassy aroma or taste of a product by adding to the product an organosulfur compound selected from prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, dimethyl sulfide, or a combination of any two or more thereof. The organosulfur compound may be added in amounts as described herein, for example from about 0.000001 wt % to about 10 wt %, from about 0.000001 wt % to about 0.6 wt %, or from about 0.000001 wt % to about 3 wt %, based on the total weight of the product. In certain embodiments, the process includes adding from about 0.000001 wt % to about 0.3 wt % of prenyl mercaptan and from about 0.000001 wt % to about 0.3 wt % of 2-methylthiophene to the product.

In certain embodiments, the process further includes adding a terpene compound to the product. Suitable terpene compounds may include the primary and secondary terpene compounds described herein. In certain embodiments, the primary terpene compound is selected from the group consisting of myrcene, β-caryophyllene, limonene, α-pinene, β-pinene, valencene, ocimene, and terpinolene. In certain embodiments, the secondary terpene compound is selected from the group consisting of humulene, linalool, α-bisabolol, nerol, α-phellandrene, α-terpineol, farnesene, fenchyl alcohol, geraniol, menthol, citronellol, citronellal, geranyl acetate, nerolidol, and citral. In certain embodiments, the primary terpene compound is added in an amount of from about 0.1 wt % to about 90 wt %, based on the total weight of the product. In certain embodiments, the secondary terpene compound is added in an amount of from about 0.01 wt % to about 10 wt %, based on the total weight of the composition.

In certain embodiments, provided herein is a process for augmenting or enhancing the gassy aroma or taste of a product selected from an edible product, an aerosol product, a fragrance product, a flavor product, and an inhalable product. The augmenting or enhancing may include adding to the product an organosulfur compound selected from prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, and dimethyl sulfide, or a combination of any two or more thereof. In certain embodiments, the edible product produced by the process is provided. In certain embodiments, the edible product is a food or beverage product. In certain embodiments, the beverage is beer, any alcohol-containing beverage, or other non-alcohol containing beverage product. In certain embodiments, the method for enhancing gassy aroma in a flavor or fragrance composition includes adding to the flavor or fragrance composition, an organosulfur compound selected from prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, and dimethyl sulfide, or combination of any two or more thereof.

Yet another aspect of the present technology relates to a method of producing a proven gassy aroma composition comprising mixing a terpene compound with an organosulfur compound selected from the group consisting of prenyl mercaptan, 2-methylthiophene and 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methyl sulfanyl)-3-methyl-2-butene), prenyl thioacetate, thiogeraniol, and dimethyl sulfide. Suitable terpene compounds may include the primary and secondary terpene compounds described herein. In certain embodiments, the primary terpene compound is selected from the group consisting of myrcene, β-caryophyllene, limonene, α-pinene, β-pinene, valencene, ocimene, and terpinolene. In certain embodiments, the secondary terpene compound selected from the group consisting of humulene, linalool, α-bisabolol, nerol, α-phellandrene, α-terpineol, farnesene, fenchyl alcohol, geraniol, menthol, citronellol, citronellal, geranyl acetate, nerolidol, and citral.

Aspects of the present technology relate to methods of breeding a cannabis plant, wherein the plant produces altered or non-natural amounts of one or more organosulfur compounds. In one embodiment, provided is a method for breeding an engineered plant, wherein said cannabis plant comprises one or more organosulfur compound, wherein the engineered cannabis plant produced greater amounts of the organosulfur compound when compared to the amount of organosulfur compound in a non-engineered or natural plant. Suitable organosulfur compounds include, but are not limited to, prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, dimethyl sulfide, or a combination of any two or more thereof. In addition to the organosulfur compound plant may also include cannabinoid active agent and a terpene compound. Suitable terpene compounds include, but are not limited to, myrcene, β-caryophyllene, α or β-Pinene, α or β-phellandrene, limonene, terpinolene, linalool, pinene, terpineol, fenchyl alcohol, α-bisabolol, camphene, terpinolene, humulene, geraniol, camphor, cedrene, 1-menthol, cis-β-ocimene, trans-β-ocimene, terpinene, delta-3-carene, isoborneol, nerol, valencene, farnesene (t), fenchone, ocimene, bergotamene, thujene, ylangene, sabinene hydrate, and the like, or a combination of any two or more thereof.

Other aspects of the present technology relate to methods for producing an organosulfur compound, wherein said method comprises cultivating a plant, wherein said plant produces an organosulfur compound selected from the group consisting of prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, dimethyl sulfide or a combination of any two or more thereof. In various embodiments, the prenyl mercaptan is produced at a concentration of from about 0.000001 wt %-10 wt %. In various embodiments, the 2-methylthiophene is produced at a concentration of from about 0.000001%-10%.

Yet other aspects of the present technology relate to method of producing a cannabis plant comprising: (i) obtaining a cannabis seed, cutting, or a plant cell, from a cannabis plant, or a clone of said cannabis plant; (ii) placing said cannabis seed, cutting, or plant cell in an environment conducive to growth; and (iii) allowing said cannabis seed, cutting, or plant cell to produce a cannabis plant, wherein the produced cannabis plant produces an altered concentration of an organosulfur compound. For example, the method may produce an engineered cannabis plant that produces greater amounts of the organosulfur compound when compared to the amount of organosulfur compound in a non-engineered or natural cannabis plant. The cannabis plant may produce an organosulfur compound content of greater than about 0.00001 μg/mg as measured by one- or two-dimensional gas chromatograph coupled with a sulfur chemiluminscence detector (GCxGC-SCD) and calculated based on dry weight of the dried, ground flower.

In certain embodiments, the engineered cannabis plant may produce one or more organosulfur compound at a concentration of from about 0.000001%-0.5%. Suitable organosulfur compounds include, but are not limited to, prenyl mercaptan, 2-methylthiophene, 3-methylthiophene, dimethyl disulfide, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, dimethyl sulfide, or a combination of any two or more thereof. In certain embodiments, the engineered cannabis plant may produce prenyl mercaptan at a concentration of from about 0.000001%-0.5%. In certain embodiments, the engineered cannabis plant may produce prenyl thioacetate at a concentration of from about 0.000001%-0.5%. The produced cannabis plant may include one or more of a cannabinoid active agent and a terpene compound.

The organosulfur compounds and terpenes described herein may be commercially sourced or can be readily prepared in a laboratory. For example, of diprenyl disulfide can be prepared via S—S coupling from prenyl mercaptan using the following synthetic scheme:

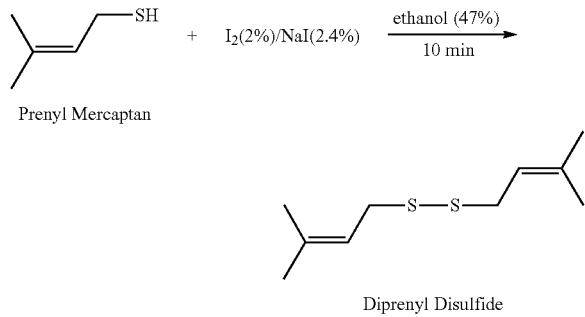

The reaction may be conducted using e.g., 2% iodine solution and about 2.4% aqueous sodium iodide solution in ethanol or in an organic solvent miscible with water. Diprenyl disulfide may also form in-situ in a composition containing prenyl mercaptan.

The present invention, thus generally described, will be understood more readily by reference to the following examples, which are provided by way of illustration and are not intended to be limiting of the present invention.

EXAMPLES

Various embodiments will be further clarified by the following examples, which are in no way intended to limit this disclosure thereto.

Example 1: Curation of Cannabis Samples

Samples of cannabis flowers were curated from different sources. All samples were stored in clear, colorless scintillation vials in a −20° C. freezer to ensure minimal loss of volatiles and decrease thermal decomposition. All samples were dried and cured prior to procurement.

Example 2: Sample Preparation 200 mg of each curated flower sample from Example 1 was transferred to 2DGC vials followed by mechanically grinding with a spatula. Vial caps were then crimped onto each vial.

Example 3: Characterization and Testing of Cultivars

Twelve cannabis cultivars were analyzed using 2-dimensional gas chromatography, mass spectrometry, and sulfur chemiluminescence to determine the chemical origin of the gassy odor in cannabis. GC x GC analysis was performed using the INSIGHT reverse fill flush flow modulator (Sepsolve Analytical) in conjunction with a 7890B GC (Agilent technologies) and BenchTOF TOF-MS (Markes International). Detection and quantification of sulfur-bearing compounds was performed using an Agilent 8355 sulfur chemiluminescence detector (SCD). Sample introduction was performed using the Centri sample preparation platform (Markes International).

Samples were incubated and agitated at a temperature of 45° C. for 10 minutes, followed by six 1 mL headspace injections from the sample vial to a cryogen free cold trap held at 25° C. After the six injections were complete, the cold trap was rapidly heated to 300° C. to desorb the sample in a narrow band onto the analytical columns. The GC x GC column configuration was a polar to apolar setup. The GC oven ramp rates used were as follows: The oven was initially set to 45° C. and held for 3 minutes. The oven was then ramped at a rate of 5° C. per minute to 90° C., followed a 2.0° C. ramp rate to 130° C., followed last by a 5° C. ramp rate to 240° C. The modulation period set for the flow modulator was 7.2 seconds.

Figure 2:
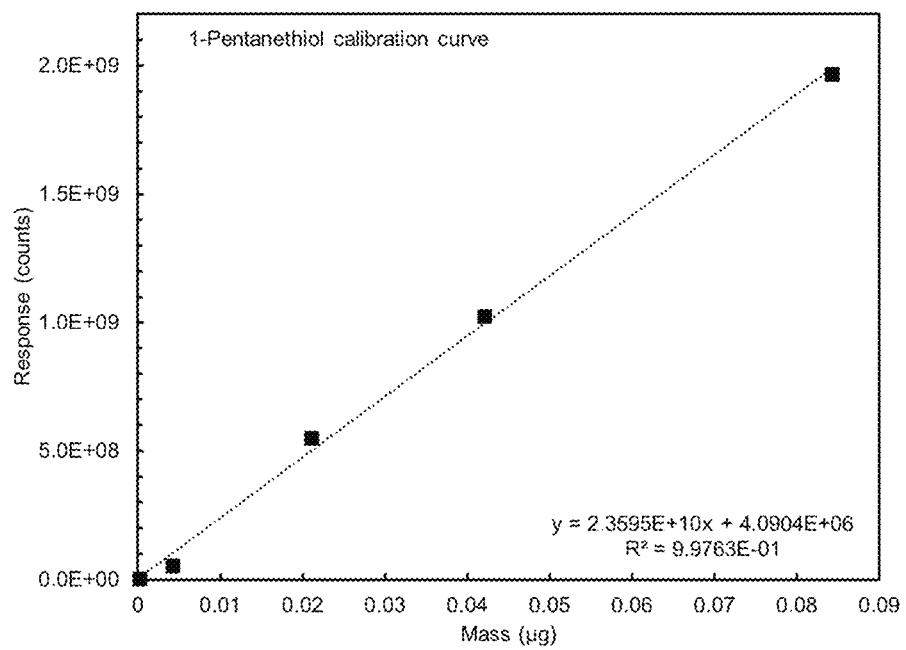
FIG. 2 shows a calibration curve of 1-pentanethiol used to obtain concentrations of prenyl mercaptan and prenyl thioacetate.

Data was collected, integrated, and analyzed using the ChromSpace software platform (Sepsolve Analytical). A 5-point calibration curve was calculated using 1-Pentanethiol (DCG Partnership I, LTD) to quantify the compounds detected from the SCD. The solutions were prepared using serial dilution of the analytical standard with pentane. As sulfur atoms provide an equimolar response to the amount present in the SCD, any analytes containing sulfur were quantified using the 1-Pentanethiol standard calibration curve. The calibration curve showing detector response versus mass is shown in FIG. 2.

Table 1 summarizes value masses used for each calibration point and the measured SCD peak volume.

TABLE 1

| Calibration point | Mass of analyte (μg) | SCD peak volume |
|---|---|---|
| 1 | 8.420E−02 | 1.967E+09 |
| 2 | 4.210E−02 | 1.026E+09 |
| 3 | 2.105E−02 | 5.502E+08 |
| 4 | 4.210E−03 | 5.485E+07 |
| 5 | 2.105E−04 | 3.759E+06 |

The cultivars were chosen with varying degrees of gassy aroma to determine the chemical origin. A clear correlation was observed between concentration of prenyl mercaptan and prenyl thioacetate (chemical structures shown in FIG. 1) in the SCD data.

Five cannabis fragrance and aroma experts were asked to rate the odors of each strain using a blind olfactory test. Table 2 summarizes the cultivars, concentrations of compounds of interest, and the organoleptic response of each flower.

TABLE 2

| Cultivar | Prenyl mercaptan mass (μg) | Prenyl thioacetate mass (μg) | Mass of flower (mg) | Concentration of Prenyl mercaptan in dry flower (μg/mg) | Concentration of Prenyl thioacetate in dry flower (μg/mg) | Organoleptic response |
|---|---|---|---|---|---|---|
| Bacio Gelato | 0.2433 | 0.0014 | 200 | 1.46E−03 | 8.49E−06 | High Gas |
| SFV OG | 0.0051 | 0.0016 | 202 | 3.01E−05 | 9.74E−06 | Moderate Gas |
| Yeti OG | 0.1007 | 0.0042 | 201 | 6.00E−04 | 2.52E−05 | High Gas |
| OG Kush | 0.0384 | 0.0022 | 201 | 2.29E−04 | 1.33E−05 | High Gas |
| Marathon OG | 0.0059 | 0.0003 | 200 | 3.51E−05 | 1.67E−06 | Moderate Gas |
| Jack Herer | Not detected | Not detected | Not detected | Not detected | Not detected | No Gas |
| Landrace sample 1 | Not detected | Not detected | Not detected | Not detected | Not detected | No Gas |
| Landrace sample 2 | Not detected | Not detected | Not detected | Not detected | Not detected | No Gas |
| Landrace sample 3 | Not detected | Not detected | Not detected | Not detected | Not detected | No Gas |
| Landrace sample 4 | Not detected | Not detected | Not detected | Not detected | Not detected | No Gas |

Figure 3:
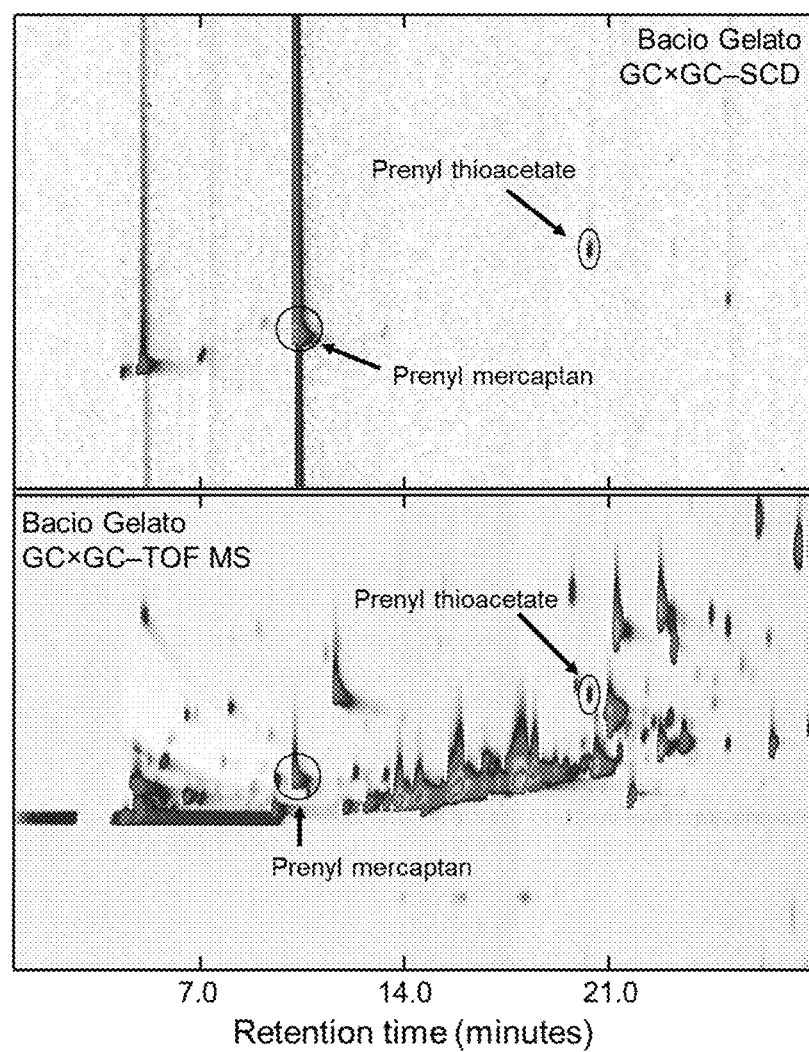
FIG. 3 represents 2-Dimensional chromatograms of the GC x GC-SCD and GC x GC-TOF-MS highlighting prenyl mercaptan and prenyl thioacetate.
Figure 4:
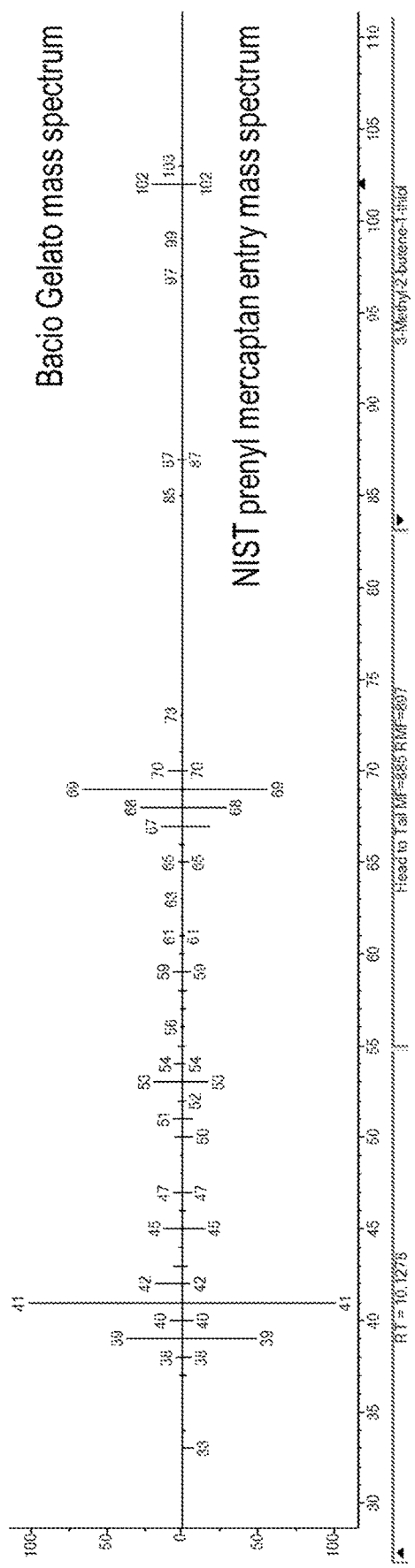
FIG. 4 shows mass spectrum of prenyl mercaptan in Bacio Gelato and mass spectrum of prenyl mercaptan obtained from the NIST mass spectral database.
Figure 5:
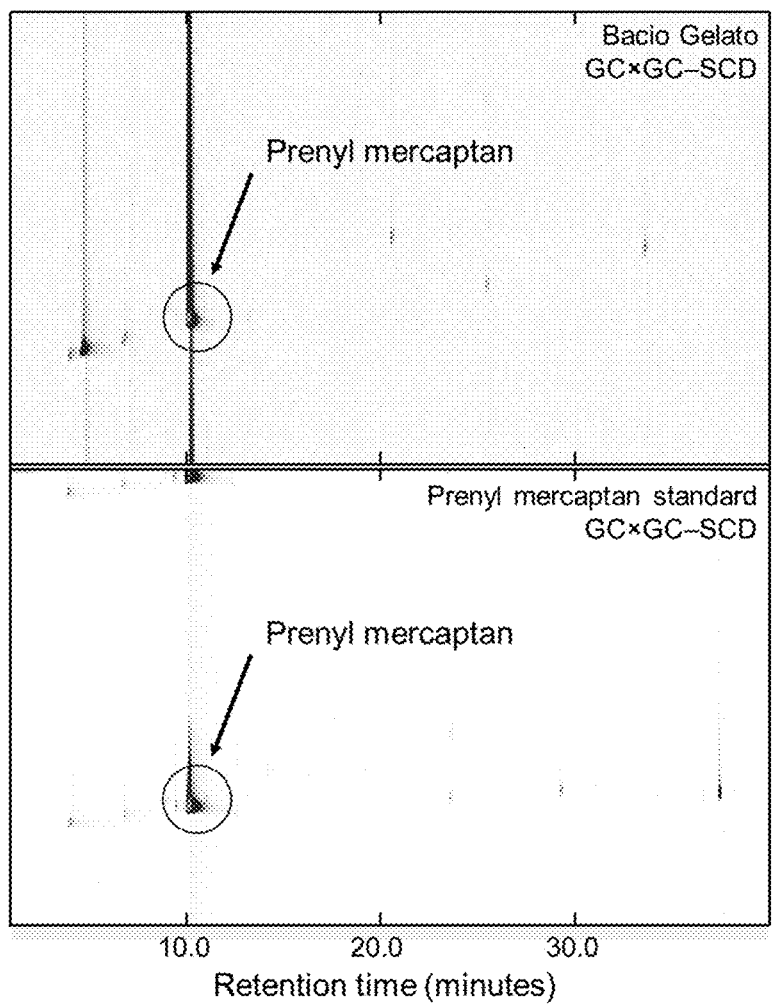
FIG. 5 represents 2-Dimensional sulfur chemiluminescence detector ("SCD") chromatograms of the GC x GC-SCD and GC x GC-TOF-MS comparing prenyl mercaptan elution in Bacio Gelato versus the standard

Of all cultivars, Bacio Gelato was found to possess the highest concentration of prenyl mercaptan as shown in Table 2. This high concentration results in an intense, piercing, gassy aroma. Prenyl thioacetate is also present in the sample, which further contributes to the aroma of this cultivar. FIG. 3 shows the 2-dimensional chromatograms for the GC x GC-SCD and GC x GC-TOF-MS data. Prenyl mercaptan elutes at $^1T_R$=10.082 minutes and $^2T_R$=2.313 seconds while prenyl thioacetate elutes at $^1T_R$=20.554 minutes and $^2T_R$=3.5943 seconds. Prenyl thioacetate has a higher second dimension retention time due to the more polar nature of the compound imparted by the acetate group. The chemical identities of the compounds of interest were determined by analyzing their mass spectral data. As prenyl mercaptan has a molar mass of 102.20 g/mol, the mass spectral peak at m/z~102 corresponds to the molecular ion. The major peak located at m/z~69 most likely corresponds to the prenyl ion $C_5H_{10}{}^+$. This is further substantiated as prenyl thioacetate also has an intense peak located at m/z~69, which also has the prenyl functional group. The final major peak is located at m/z~41, which most likely corresponds to the $C_3H_6{}^+$ fragment. The spectrum obtain from the experimental data was then compared with that provided by the NIST Spectral Library v17 (2017), and Wiley Registry of Mass Spectra (11$^{th}$ Edition) which showed excellent match with prenyl mercaptan (FIG. 4). Lastly, data on a prenyl mercaptan standard (Excellentia, 1% in triacetin) confirmed the elution retention times in the 2-dimensional data (FIG. 5). The aroma of the prenyl mercaptan standard was extremely pungent even at 1% concentration in triacetin indicating a very low olfactory response. A 10-fold dilution was conducted which resulted in a similar aroma to that in the Bacio Gelato flower, further confirming the importance of prenyl mercaptan towards the gassy aroma.

Example 4: Identification of Other Aroma Compounds

Figure 6:
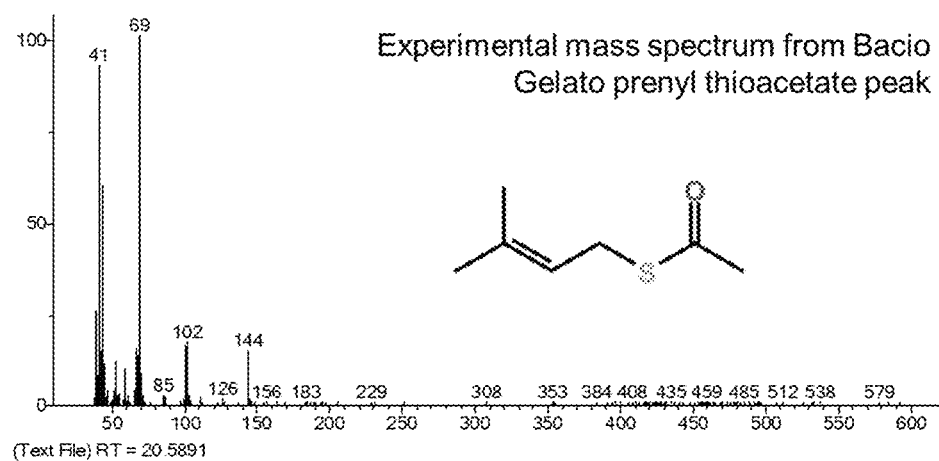
FIG. 6 shows mass spectrum of prenyl thioacetate in Bacio Gelato and a standard sample, both showing the peak for prenyl thioacetate at $^1T_R$=20.554 minutes and $^2T_R$=3.5943 seconds.
Figure 6:
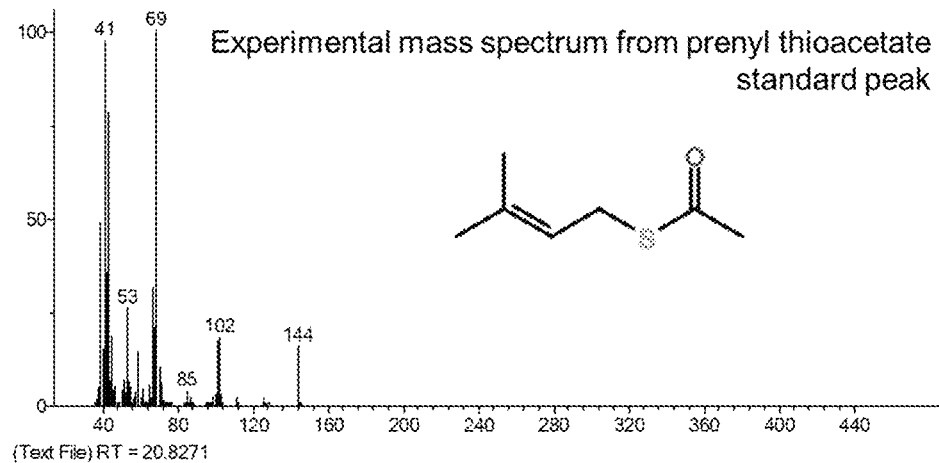
Figure 7:
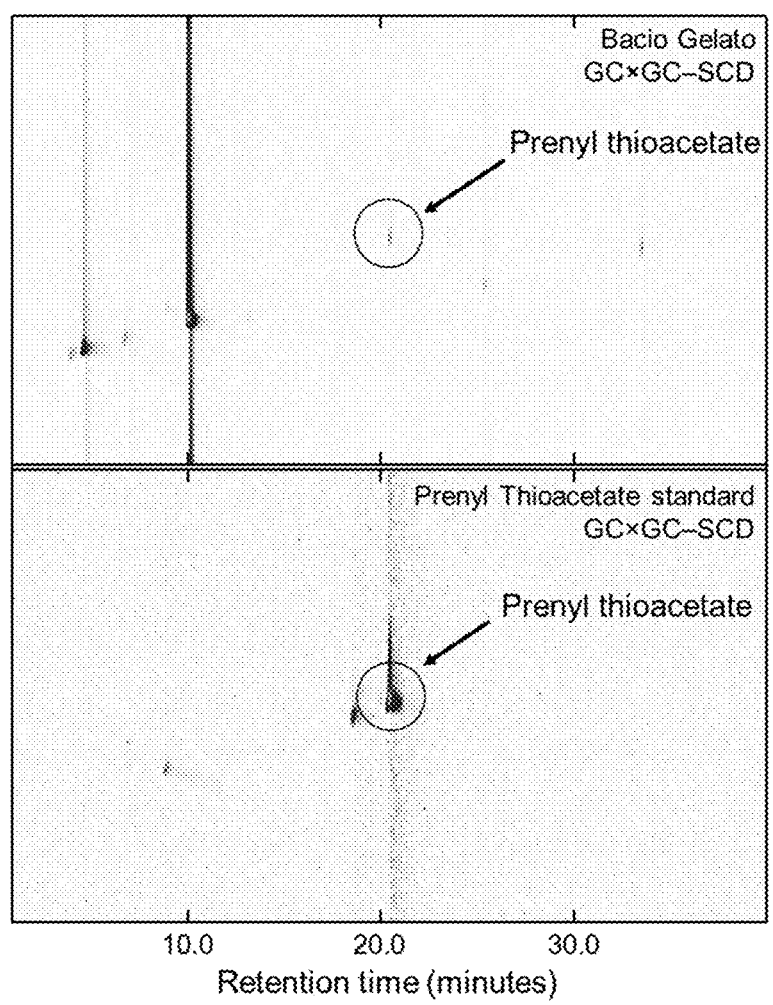
FIG. 7 represents 2-Dimensional sulfur chemiluminescence detector ("SCD") chromatograms of the GC x GC-SCD and GC x GC-TOF-MS comparing prenyl thioacetate elution in Bacio Gelato versus the standard.

A second eluent of interest in the SCD data suggested a compound with similar functionality based on the mass spectral data (FIG. 6). The eluent with retention times of $^1T_R$=20.554 minutes and $^2T_R$=3.5943 seconds contains the same major ions m/z=41, 69 and 102, indicating the prenyl functionality most likely exists in this compound as well as the molecular fragment $C_5H_{10}S^{\pm}$. However, the largest m/z ratio is located at ~144, suggesting a larger compound with more functionality than prenyl mercaptan. Additionally, the higher second dimension retention time than prenyl mercaptan (3.5943 and 2.313 seconds, respectively) indicates greater polarity and presence of electronegative atoms such as oxygen. Based on the mass spectral data and the location in the 2-dimensional chromatograms, the formula was indicated to be $C_7H_{12}OS$, which would yield the structure of 3-methyl-2-butenyl acetothioate, or prenyl thioacetate (CAS #33049-93-3). A comparison with a standard sample of prenyl thioacetate (Toronto Research Chemicals, 97%) indicated that the major eluent appears at the same retention times as the unknown in Bacio Gelato (FIG. 7), confirming that the unknown in gassy cannabis samples is prenyl thioacetate. The aroma of the prenyl thioacetate standard was observed to be similar to prenyl mercaptan but had a slightly sharper scent, confirming that this compound also contributes to the gassy aroma in cannabis.

Figure 8:
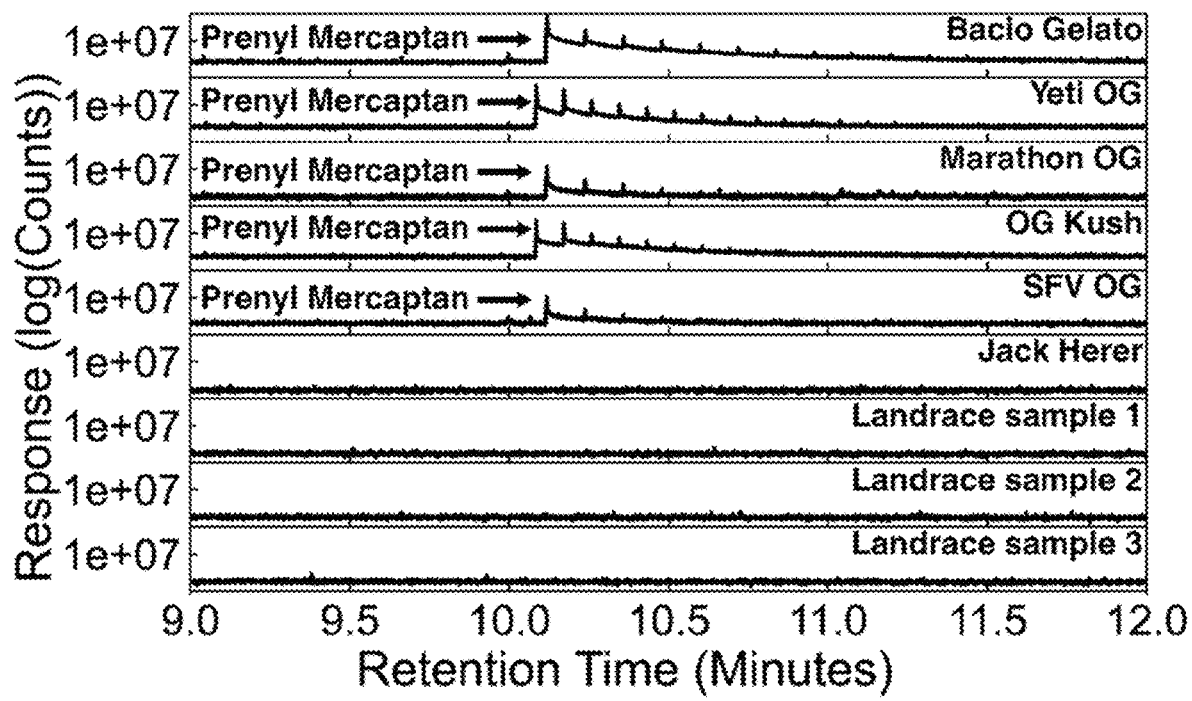
FIG. 8 represents 1-Dimensional sulfur chemiluminescence detector ("SCD") chromatograms of selected strains showing the differences in concentration of prenyl mercaptan (~10.2 minutes) in gassy and non-gassy cultivars.
Figure 9:
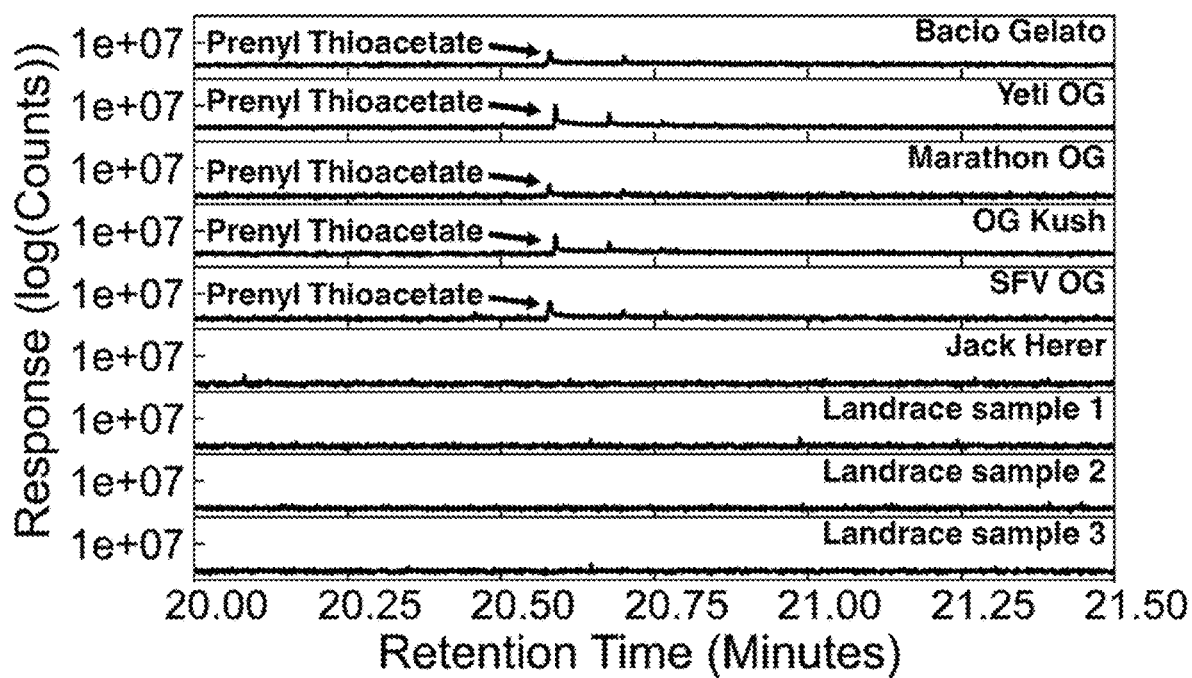
FIG. 9 represents 1-Dimensional sulfur chemiluminescence detector ("SCD") chromatograms of selected strains showing the differences in concentration of prenyl thioacetate (~10.2 minutes) in gassy and non-gassy cultivars.

The remaining cultivars were screened for the presence of prenyl thioacetate and their respective concentrations as shown in Table 2. FIG. 8 shows the SCD 1-D chromatograms of the 2-dimensional data to illustrate the differences in prenyl mercaptan in high-gas and low-gas samples. A clear trend was observed such that cultivars with a gassy aroma have detectable peaks, and therefore higher concentrations, of prenyl mercaptan. A similar trend was also established for prenyl thioacetate, where the compound was present in cultivars with a gassy aroma (FIG. 9). Cultivars that had no detectable concentrations of these compounds had no appreciable gassy aroma.

These results confirm the origins of the gassy odor in cannabis and explain how the aroma can be modulated through coupling of other compounds present in the cannabis plant.

Example 5: Preparation and Testing of Blends

The following blend compositions, namely, Composition A, Composition B, Composition C and Composition D, and were prepared for their prenyl mercaptan and 2-methylthiophene content as well as other components. The compositions are summarized in Table 3.

TABLE 3

| Compound (wt %) | Composition A | Composition B | Composition C | Composition D |
|---|---|---|---|---|
| prenyl mercaptan | 0.076 | 0.0454 | 0.031 | 0.045 |
| triacetin | 7.324 | 4.386 | 3.04 | 4.386 |
| 2-methylthiophene (1% in D-limonene) | 0.002 | 0.0012 | 0.033 | 0.001 |
| Dimethyl Disulfide (1% in D-limonene) | 0.002 | 0.0014 | — | 0.001 |
| D-Limonene | 27.903 | 24.086 | 22.64 | 24.115 |
| Myrcene | 22.012 | 20.88 | 59.66 | 20.946 |
| β-Caryophyllene | 18.985 | 16.99 | 2.38 | 17.846 |
| Linalool | 6.292 | 5.39 | 2.27 | 5.665 |
| β-Pinene | 5.05 | 4.94 | 1.74 | 5.19 |
| Alpha-Terpineol | 2.686 | 2.34 | 0.35 | 2.46 |
| Alpha-Pinene | 2.557 | 3.19 | 3.12 | 3.348 |
| Fenchyl Alcohol | 2.465 | 5.46 | 0.58 | 5.733 |
| Alpha-Bisabolol | 1.775 | 1.6 | 0.02 | 1.676 |
| Camphene | 0.754 | 0.66 | 1.37 | 0.692 |
| Terpinolene | 0.699 | 2.2 | 0.49 | 2.31 |
| Alpha-Humulene | 0.313 | 2.33 | 0.57 | — |
| Geraniol | 0.294 | 0.26 | 0.0031 | 0.277 |
| Camphor | 0.258 | 1.18 | 0.0027 | 1.24 |
| Alpha-Cedrene | 0.166 | 0.16 | 0.0017 | — |
| L-Menthol | 0.074 | 0.07 | 0.0008 | 0.078 |
| Cis-ocimene | 0.055 | 0.06 | 0.0006 | — |
| Sabinene Hydrate | 0.055 | 0.06 | 0.0006 | 0.064 |
| Trans-ocimene | 0.055 | 0.33 | 0.0006 | 0.403 |
| Alpha-Phellandrene | 0.037 | 0.11 | 0.0004 | 0.114 |
| Alpha-Terpinene | 0.037 | 0.08 | 0.15 | 0.081 |
| Delta-3-Carene | 0.037 | 2.97 | 0.0004 | 3.115 |
| Isoborneol | 0.037 | 0.04 | 0.0004 | 0.041 |
| Nerol | — | 0.01 | — | 0.002 |
| Valencene | — | 0.04 | 0.22 | 0.042 |
| Farnesene (t) | — | 0.13 | 0.12 | 0.134 |
| Fenchone | — | — | 0.17 | — |
| Ethyl Isobutyrate | — | — | 0.003 | — |
| Hexanal | — | — | 0.016 | — |
| Hexyl Caproate | — | — | 0.04 | — |
| 2-Heptanone | — | — | 0.01 | — |
| n-Hexyl butanoate | — | — | 0.01 | — |
| Pyrazine, 2,5-dimethyl- | — | — | 0.01 | — |
| Ylang | — | — | 0.56 | — |
| Alpha-methyl butanal | — | — | 0.11 | — |
| Bergotamene | — | — | 0.086 | — |
| Ocimene | — | — | 0.067 | — |
| Alpha-Thujene | — | — | 0.06 | — |
| 1-Hexanol | — | — | 0.057 | — |
| DiPrenyl DiSulfide | — | — | 0.052 | — |
| Prenyl Thioacetate | — | — | 0.027 | — |

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth). Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like, include the number recited and refer to ranges which may be subsequently broken down into subranges as discussed above. Finally, as will be understood by one skilled in the art, a range includes each individual member. Thus, for example, a group having 1-3 layers refers to groups having 1, 2, or 3 layers. Similarly, a group having 1-5 layers refers to groups having 1, 2, 3, 4, or 5 layers, and so forth.

The drawings shall be interpreted as illustrating one or more embodiments that are drawn to scale and/or one or more embodiments that are not drawn to scale. This means the drawings may be interpreted, for example, as showing: (a) everything drawn to scale, (b) nothing drawn to scale, or (c) one or more features drawn to scale and one or more features not drawn to scale. Accordingly, the drawings can serve to provide support to recite the sizes, proportions, and/or other dimensions of any of the illustrated features either alone or relative to each other. Furthermore, all such sizes, proportions, and/or other dimensions are to be understood as being variable from 0-100% in either direction and thus provide support for claims that recite such values or any and all ranges or subranges that may be formed by such values.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean," etc.). References to specific examples, use of "i.e.," use of the word "technology," etc., are not meant to invoke exception (b) or otherwise restrict the scope of the recited claim terms. Other than situations where exception (b) applies, nothing contained in this document should be considered a disclaimer or disavowal of claim scope.

Unless otherwise defined, all terms (including technical and scientific terms) used herein have the same meaning as commonly understood by one of ordinary skill in the art to which this technology belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

In addition, where features or aspects of the disclosure are described in terms of Markush groups, those skilled in the art will recognize that the disclosure is also thereby described in terms of any individual member or subgroup of members of the Markush group.

Unless the context indicates otherwise, it is specifically intended that the various features of the technology described herein may be used in any combination. Moreover, the disclosure also contemplates that in certain embodiments, any feature or combination of features set forth herein may be excluded or omitted. To illustrate, if the specification states that a complex comprises components A, B and C, it is specifically intended that any of A, B or C, or a combination of any two or more thereof, may be omitted and disclaimed singularly or in any combination.

Unless explicitly indicated otherwise, all specified embodiments, features, and terms intend to include both the recited embodiment, feature, or term and biological equivalents thereof.

All patents, patent applications, provisional applications, and publications referred to or cited herein are incorporated by reference in their entirety, including all figures and tables, to the extent they are not inconsistent with the explicit teachings of this specification.

Other embodiments are set forth in the following claims.

What is claimed is:

1. A method for producing a composition with a gassy aroma, the method comprising:
   mixing a terpene compound with an organosulfur compound to form a composition;
   wherein:
      the organosulfur compound comprises prenyl mercaptan, 2 methylthiophene, 3 methylthiophene, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), prenyl thioacetate, thiogeraniol, or a mixture of any two or more thereof; and
      the terpene compound comprises myrcene, β-caryophyllene, limonene, α-pinene, β-pinene, valencene, ocimene, terpinolene, humulene, linalool, bisabolol, nerol, phellandrene, terpineol, farnesene, fenchyl alcohol, geraniol, menthol, citronellol, citronellal, geranyl acetate, nerolidol, citral, or a mixture of any two or more thereof;
   wherein:
      the composition comprises about 0.000001 wt % to about 0.3 wt % of the organosulfur compound, based on a total weight of the composition; and
      the composition is an edible composition, an aerosol composition, a flavor composition, a fragrance composition, or an inhalable composition.

2. The method of claim 1, wherein the organosulfur compound comprises prenyl mercaptan, prenylthioacetate, or 2-methylthiophene.

3. The method of claim 1, wherein the terpene compound is present in the composition from about 0.1 wt % to about 99 wt %, based on the total weight of the composition.

4. The method of claim 3, wherein the terpene compound is present in the composition from about 0.01 wt % to about 50 wt %, based on the total weight of the composition.

5. The method of claim 1, wherein the composition is an edible composition.

6. The method of claim 5, wherein the edible composition is a food or a beverage.

7. The method of claim 6, wherein the beverage is beer, an alcohol containing beverage, or a non-alcohol containing beverage product.

8. The method of claim 1, wherein the composition is an inhalation composition.

9. The method of claim 1, wherein the composition is a flavor and/or fragrance composition.

10. The method of claim 1, wherein the organosulfur compound comprises prenyl mercaptan, diprenyl disulfide, 3-methyl-2-buten-1-yl thiolacetate, 3-methyl-1-[(3-methyl-2-buten-1-yl)sulfanyl]-2-butene, prenylmethylthiol (1-(methylsulfanyl)-3-methyl-2-butene), or prenyl thioacetate; and the terpene compound comprises myrcene, limonene, α-pinene, β-pinene, valencene, ocimene, terpinolene, linalool, bisabolol, nerol, phellandrene, terpineol, farnesene, fenchyl alcohol, geraniol, menthol, citronellol, citronellal, geranyl acetate, nerolidol, or citral.

11. The method of claim 1, wherein the organosulfur compound comprises prenyl mercaptan or prenyl thioacetate.

12. The method of claim 1, wherein the terpene compound is a mixture of any two or more of the terpene compounds, and the organosulfur compound is a mixture of any two or more of the sulfur compounds.

* * * * *